(12) United States Patent
Reid

(10) Patent No.: US 8,845,332 B1
(45) Date of Patent: Sep. 30, 2014

(54) INTERACTIVE HEIGHT MEASUREMENT SYSTEM

(76) Inventor: Donald J. Reid, Smithtown, NY (US)

( * ) Notice: Subject to any disclaimer, the term of this patent is extended or adjusted under 35 U.S.C. 154(b) by 109 days.

(21) Appl. No.: 13/409,396

(22) Filed: Mar. 1, 2012

(51) Int. Cl.
*G09B 19/00* (2006.01)
*A61B 5/107* (2006.01)
*G01G 19/00* (2006.01)

(52) U.S. Cl.
CPC .................................. *A61B 5/1072* (2013.01)
USPC .............. 434/127; 33/512; 702/166; 702/173

(58) Field of Classification Search
USPC ....................... 434/127; 33/512; 702/166, 173
See application file for complete search history.

(56) References Cited

U.S. PATENT DOCUMENTS

| | | | |
|---|---|---|---|
| 4,008,524 A | 2/1977 | Allen | |
| D259,925 S | 7/1981 | Palmer | |
| D279,358 S | 6/1985 | Lichtman | |
| 5,379,028 A * | 1/1995 | Chung | 340/692 |
| 6,073,359 A | 6/2000 | Lee | |
| D460,366 S | 7/2002 | Winter | |
| 7,155,838 B2 | 1/2007 | Leyden et al. | |
| D617,665 S | 6/2010 | Colonna | |
| 7,910,840 B2 | 3/2011 | Chai | |
| 8,109,008 B1 * | 2/2012 | Niemczak et al. | 33/832 |
| 2010/0051353 A1 | 3/2010 | Swan | |

* cited by examiner

*Primary Examiner* — Timothy Musselman
*Assistant Examiner* — Elroy S Crocker

(57) ABSTRACT

An educational and interactive system for teaching children the importance of maintaining proper nutrition in order to induce healthy growth utilizing an interactive audio system that updates a child regarding the child's height and outputs pre-recorded messages. A system having an elongate member adapted to determine accurate height measurements of a child, the elongate member having a measurement indicator extending from the top of the face of the elongate member to the bottom of the face of the elongate member, the elongate member with a series of food decals disposed at predetermined locations on the face of the elongate member.

6 Claims, 4 Drawing Sheets

(Back ISO View)

(Front Extended View)

(Side View)

(Front View)

(Block Diagram)

INTERACTIVE HEIGHT MEASUREMENT SYSTEM

BACKGROUND OF THE INVENTION

The present invention relates to systems and devices for determining measurements of a human, or, more particularly, a child or adolescent teenager.

SUMMARY

The present invention features an educational and interactive height measurement system for young adults and children. In some embodiments, the system comprises a microprocessor, power source, audio system, a series of control buttons, a measurement indicator, an elongate member and a stand, a plurality of sensors and a communication port.

Children and young adults are notorious, especially in the United States, for avoiding proper nutrition and consumption of vital nutrients and minerals obtained from vegetables and other foods. Despite their best efforts, many parents have been unsuccessful in persuading children to consume nutritional foods at a young age.

As such, there is a need for a fun, interactive and educational system to teach young adults to consume proper foods by tracking height measurements and changes in said measurements over time, thereby teaching said young adults that consumption of proper foods is required for natural and healthy growth.

In some embodiments the present invention features an interactive system allowing children to track their height measurements over time. Where a child interacts with the system, the system can be configured to ask the child whether or not the child has consumed vegetables or other nutritional foods when the system reports to the child whether or not the height of the child has changed.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

DESCRIPTION OF PREFERRED EMBODIMENTS

Figure 1:
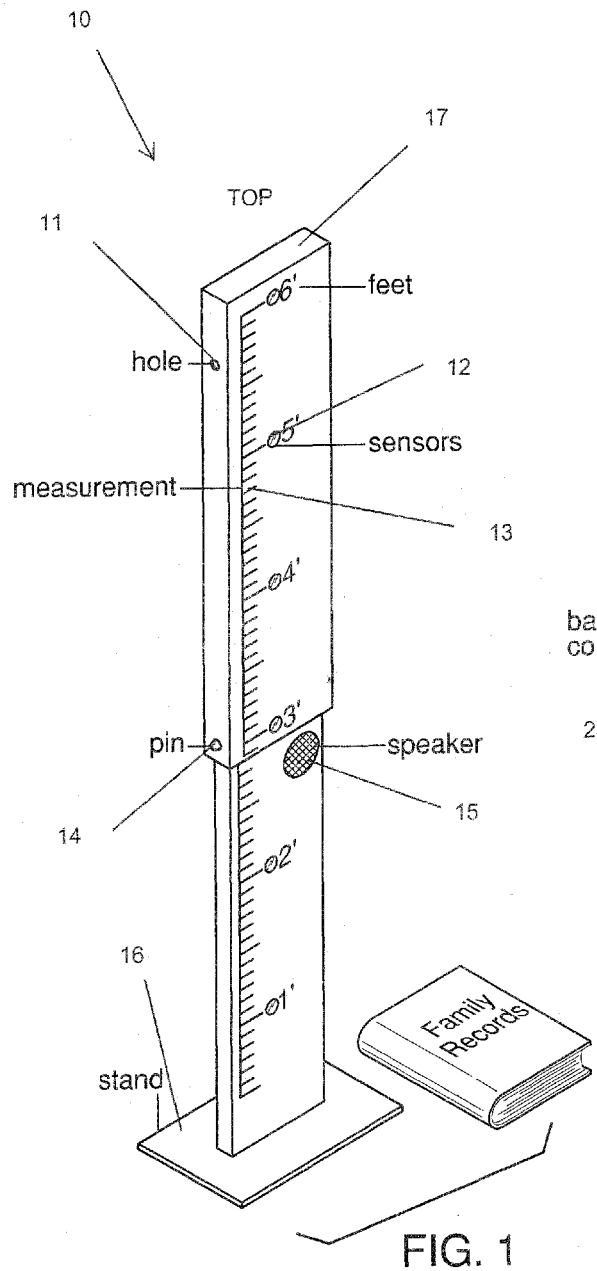
FIG. 1 is a angled front view of the present invention.
Figure 2:
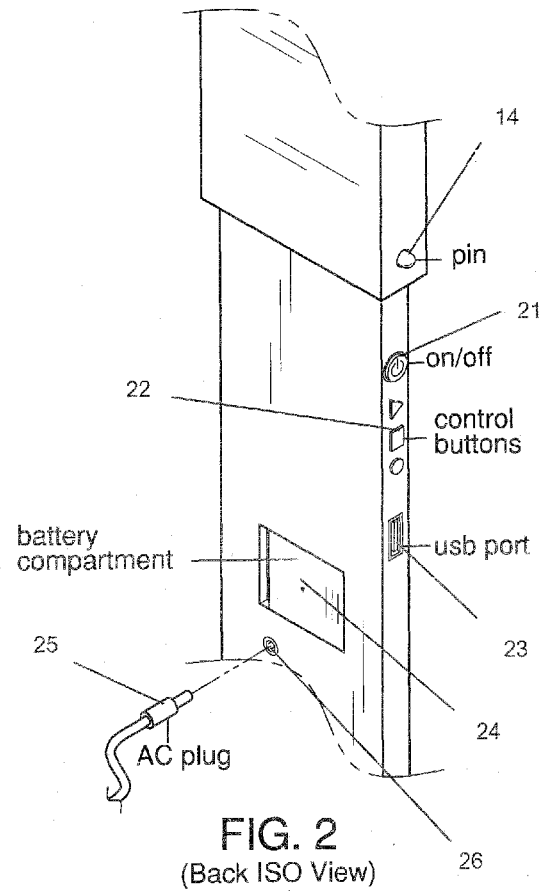
FIG. 2 is a back isometric ("ISO") view of the present invention.
Figure 3:
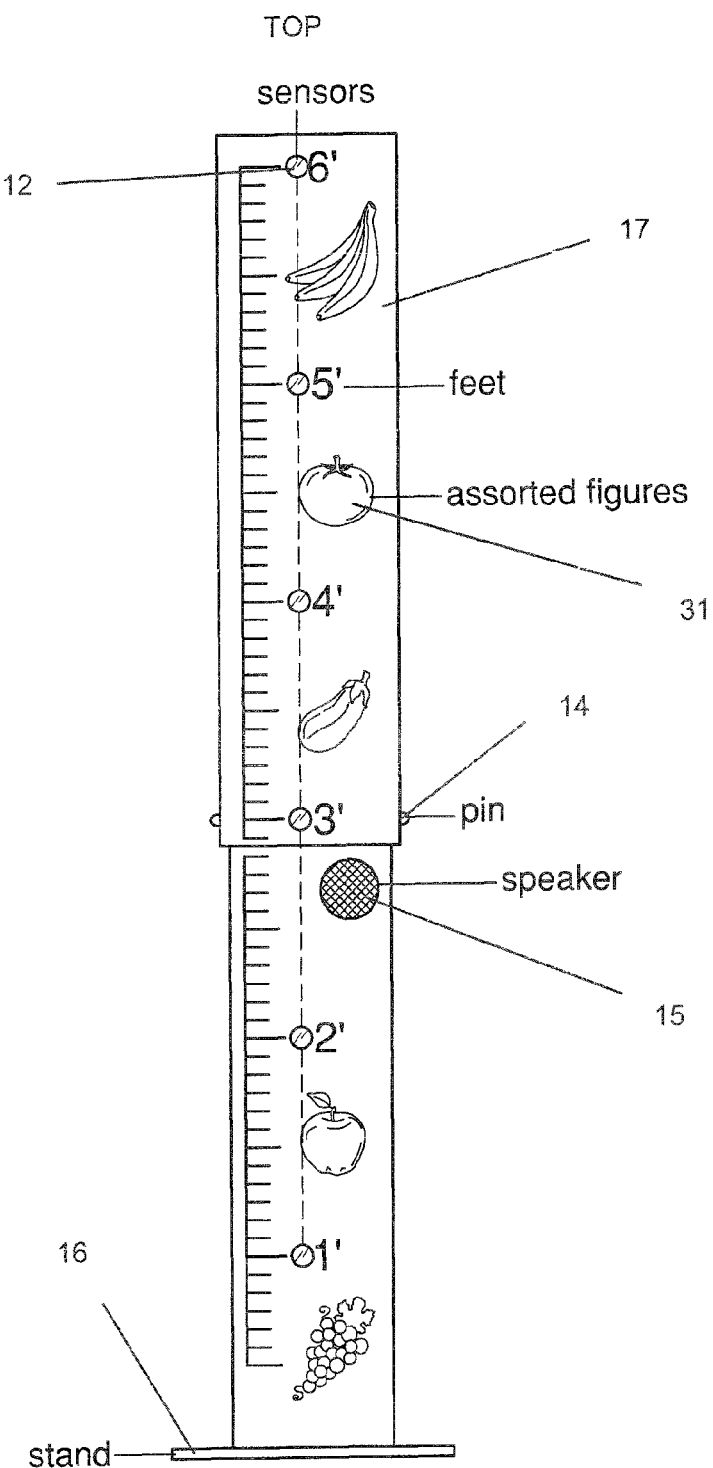
FIG. 3 is a front extended view of the present invention.
Figure 4:
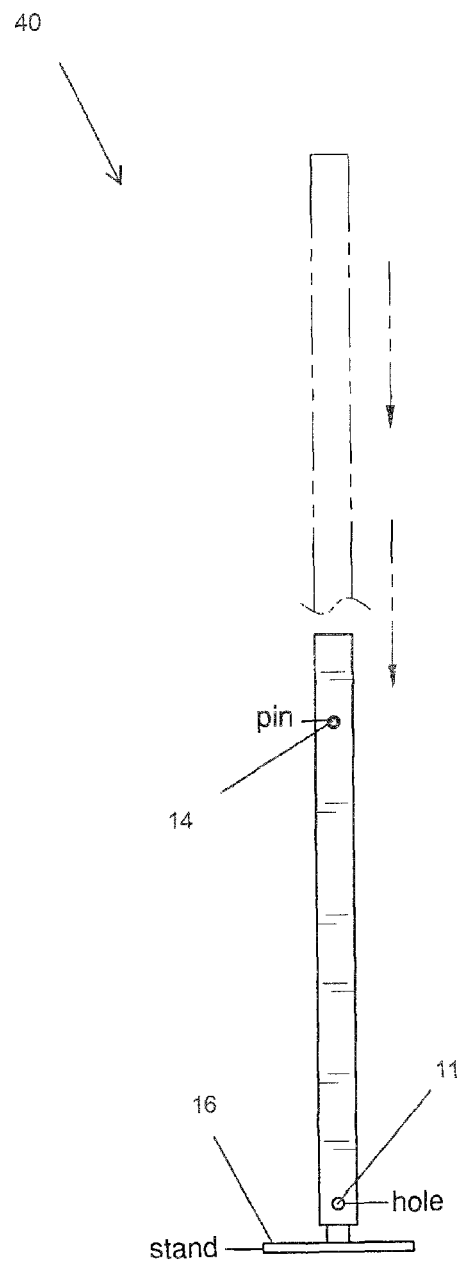
FIG. 4 is a side view of the present invention.
Figure 5:
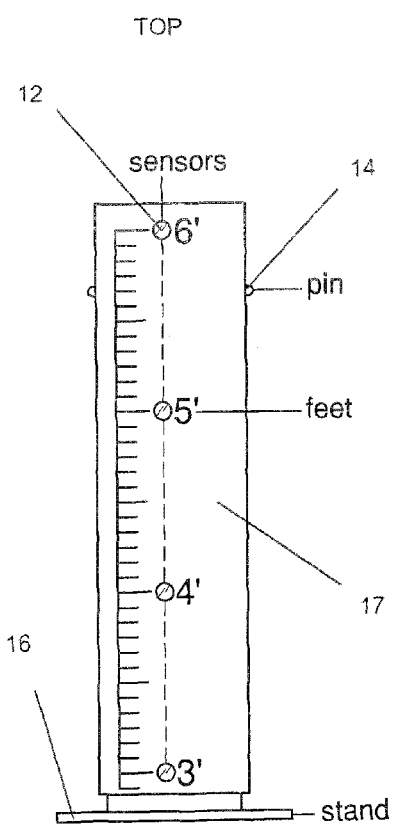
FIG. 5 is a front view of the present invention.
Figure 6:
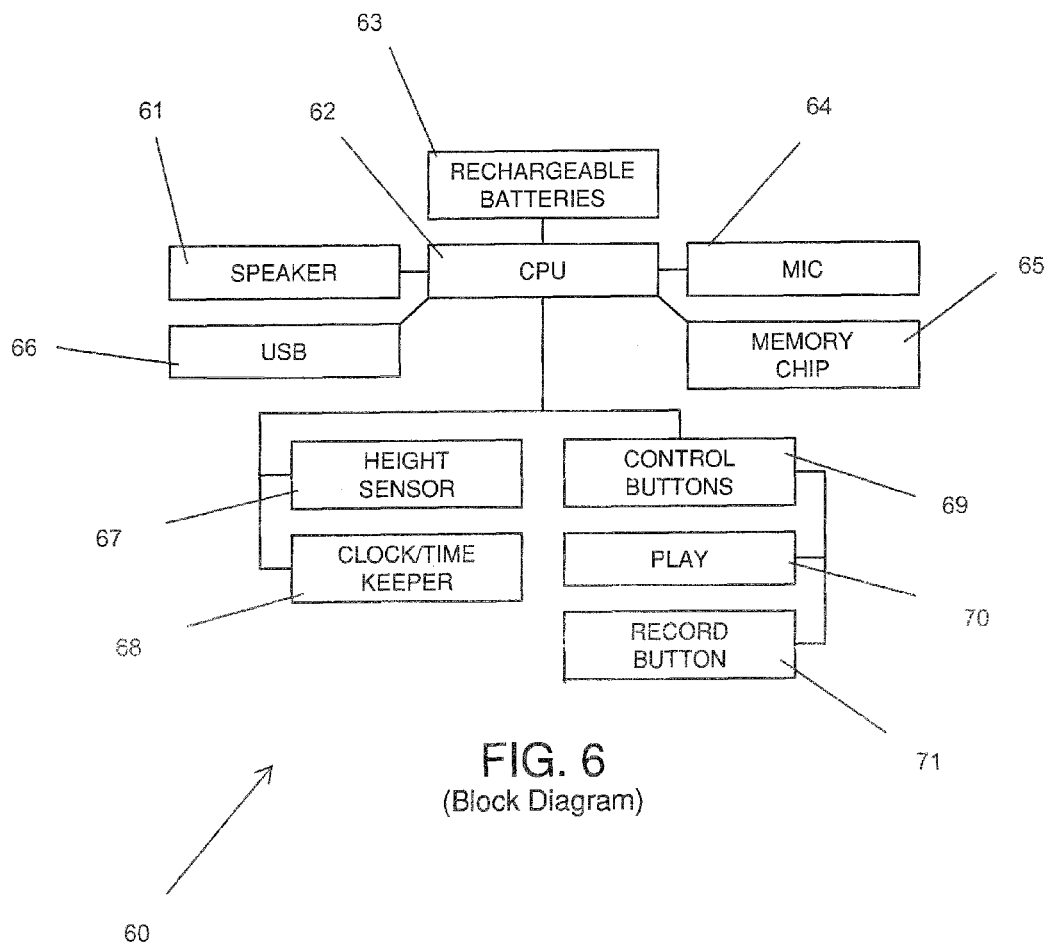
FIG. 6, is a block diagram view of the present invention illustrating the communication network between the various electrical components claimed and used in the present invention.

Referring now to FIG. 1-6, the present invention features, in some embodiments, an educational and interactive system for teaching children the importance of maintaining proper nutrition in order to induce healthy growth. The present invention can comprise the following components.

First, an elongate member [17] adapted to determine accurate height measurements of a child, the elongate member [17] comprising a measurement indicator [13] extending from the top of the face of the elongate member [17] to the bottom of the face of the elongate member [17], the elongate member [17] further comprising a series of food decals [31] disposed at predetermined locations on the face of the elongate member [17].

Second, a stand [16], fixedly attached to the elongate member [17] such that the stand [16] and the elongate member [17] are in perpendicular alignment and where the bottom of the stand [16] is flush with a floor surface, said stand configured to support the weight of the child.

Third, a microprocessor [62], the microprocessor [62] disposed within the elongate member [17], where the microprocessor is configured to process and output data received through a series of control buttons [22], the microprocessor [62] further configured to process and output data received from a plurality of sensors [12], and where the microprocessor [62] is configured to transmit audio signals.

Fourth, a storage medium [65], the storage medium [65] disposed at a predetermined location within the elongate member [17], the storage medium [65] in electronic communication with the microprocessor [62], wherein the storage medium [65] is configured to communicate with the microprocessor [62] and store or retrieve information, received from the microprocessor [62], regarding height measurements of the child and changes in the child's height.

Fifth, the plurality of sensors [12], the sensors disposed at predetermined locations along the outside of the elongate member [17] and in substantial alignment with the measurement indicator [13] such that each sensor [12] is disposed in a position adjacent to a corresponding measurement mark on the measurement indicator [13], wherein the sensors [12] are in electronic communication with the microprocessor [62] and said sensors [12] are adapted to transmit data to the microprocessor [62] about the height of the child interacting with the system, wherein each of the sensors [12] are configured to signal a positive reading to the microprocessor [62] when any portion of the child's body covers one of the sensors [12], and wherein the height of the child is determined by the sensor [12] disposed closest from the top of the elongate member [17] that signals a positive reading.

Sixth, a power source [24], the power source [24] disposed at a predetermined location within the elongate member [17] wherein the power source [24] provides power to the system, the power source [24] activated and deactivated via a power switch [21].

Seventh, a communication port [23], disposed at a predetermined location on the outside of the elongate member [17] and in electronic communication with the microprocessor [62], the communication port [23] configured to input and output data to and from the system.

Eighth, an interactive audio system, the audio system in electronic communication with the microprocessor [62], the audio system comprising an output speaker [15] disposed on the face and substantially centermost portion of the elongate member [17] whereupon receiving audio signals from the microprocessor [62], the audio system is configured to output, via the speaker [15], corresponding sound messages to the child about the child's height and changes in the child's height as determined by the plurality of sensors [12], and wherein the audio system is further configured to output prerecorded sound messages to the speaker [15].

In some embodiments, the child activates the system by engaging the power source [24], using the power switch [21], whereby the child stands on the stand [16] and positions his or her head against the face of the elongate member [17]. Thereafter, the sensors [12] transmit data corresponding to the height of the child to the microprocessor [62], whereby if the child has previously interacted with the system, the microprocessor sends an information request to the storage medium [65] to request information about previous height measurements and the microprocessor [62] calculates any changes in the child's height. Next, the microprocessor [62] sends a predetermined output signal to the audio system and the audio system outputs a pre-recorded audio message to the child via the speaker [15].

As used herein, the term "about" refers to plus or minus 10% of the referenced number.

As used herein, the term "about" refers to plus or minus 10% of the referenced number. For example, an embodiment wherein the device is about 10 inches in length includes a device that is between 9 and 11 inches in length.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

The reference numbers recited in the below claims are solely for ease of examination of this patent application, and are exemplary, and are not intended in any way to limit the scope of the claims to the particular features having the corresponding reference numbers in the drawings.

What is claimed is:

1. An educational and interactive system for teaching children the importance of maintaining proper nutrition in order to induce healthy growth, the system comprising:
   (a) a collapsible elongate member adapted to determine accurate height measurements of a child, wherein the elongate member comprises a first, top half of the elongate member and a second, bottom half of the elongate member, wherein the second half is connected to a stand, wherein the first half collapses over an outer surface of the second half, the elongate member comprising a measurement indicator extending from a top of a face of the elongate member to a bottom of the face of the elongate member, the elongate member further comprising a series of food decals disposed at predetermined locations on the face of the elongate member;
   (b) the stand, fixedly attached to the elongate member such that the stand and the elongate member are in perpendicular alignment and where the bottom of the stand is flush with a floor surface, said stand configured to support the weight of the child;
   (c) a microprocessor, the microprocessor disposed within the elongate member, where the microprocessor is configured to process and output data received through a series of control buttons, the microprocessor further configured to process and output data received from a plurality of sensors, and where the microprocessor is configured to transmit audio signals;
   (d) a storage medium, the storage medium disposed at a predetermined location within the elongate member, the storage medium in electronic communication with the microprocessor, wherein the storage medium is configured to communicate with the microprocessor and store or retrieve information, received from the microprocessor, regarding height measurements of the child and changes in the child's height;
   (e) the plurality of sensors, the sensors disposed at predetermined locations along the outside of the elongate member and in substantial alignment with the measurement indicator such that each sensor is disposed in a position adjacent to a corresponding measurement mark on the measurement indicator, wherein the sensors are in electronic communication with the microprocessor and said sensors are adapted to transmit data to the microprocessor about the height of the child interacting with the system, wherein each of the sensors are configured to signal a positive reading to the microprocessor when any portion of the child's body covers one of the sensors, and wherein the height of the child is determined by the sensor disposed closest from the top of the elongate member that signals a positive reading;
   (f) a power source, the power source disposed at a predetermined location within the elongate member wherein the power source provides power to the system, the power source activated and deactivated via a power switch;
   (g) a communication port, disposed at a predetermined location on the outside of the elongate member and in electronic communication with the microprocessor, the communication port configured to input and output data to and from the system;
   (h) an interactive audio system, the audio system in electronic communication with the microprocessor, the audio system comprising an output speaker disposed on the face and substantially centermost portion of the elongate member whereupon receiving audio signals from the microprocessor, the audio system is configured to output, via the speaker, corresponding sound messages to the child about the child's height and changes in the child's height as determined by the plurality of sensors, and wherein the audio system is further configured to output prerecorded sound messages to the speaker,
wherein the child activates the system by engaging the power source, using the power switch, whereby the child stands on the stand and positions his or her head against the face of the elongate member, whereby the sensors transmit data corresponding to the height of the child to the microprocessor, whereby if the child has previously interacted with the system, the microprocessor sends an information request to the storage medium to request information about previous height measurements and the microprocessor calculates any changes in the child's height, whereby the microprocessor sends a predetermined output signal to the audio system and whereby the audio system outputs a pre-recorded audio message to the child via the speaker.

2. The elongate member of claim 1, the first half having a connection point at a predetermined location on the bottom portion of the first half, the second half having a complimentary connection point located on the top portion of the second half, wherein the first half and second half can be connected by aligning the connection point and the complimentary connection point, creating the elongate member.

3. The communication port of claim 1, wherein the communication port comprises a Universal Serial Bus ("USB") port, Ethernet port, Mini USB, Micro USB, or wireless network card.

4. The power source of claim 1, wherein the power source comprises rechargeable batteries and electrical wiring.

5. The speaker system of claim 1, wherein the speaker system further comprises a microphone disposed at a predetermined location on the elongate member, said microphone in electronic communication with the microprocessor and power source, said microphone configured to input information regarding the vocal characteristics of a parent or other person.

6. The audio system of claim 1, wherein the audio system further comprises a microphone disposed at a predetermined location on the elongate member, said microphone in electronic communication with the microprocessor and power source, said microphone and the microprocessor configured for inputting and processing voice commands in order to substitute for the series of control buttons so that the child can activate and interact with the system using the voice commands.

* * * * *